United States Patent [19]

Sowerby et al.

[11] Patent Number: 5,712,885

[45] Date of Patent: Jan. 27, 1998

[54] DETERMINATION OF PRE-REDUCTION DEGREE IN IRON ORE MATERIALS

[75] Inventors: Brian David Sowerby, Kareela; Cheryl Su-Lean Lim, Heathcote, both of Australia

[73] Assignee: Commonwealth Scientific and Industrial Research Organisation, Australian Capital Territory, Australia

[21] Appl. No.: 475,858

[22] Filed: Jun. 7, 1995

[30] Foreign Application Priority Data

Jun. 9, 1994 [AU] Australia ............... PM6167

[51] Int. Cl.⁶ ...................................... G21G 1/06
[52] U.S. Cl. ...................................... 376/159
[58] Field of Search ........................ 376/159, 158; 250/390.04

[56] References Cited

U.S. PATENT DOCUMENTS 3,812,364  5/1974  Higatsberger et al. .............. 376/159

Primary Examiner—Daniel D. Wasil
Attorney, Agent, or Firm—Merchant, Gould, Smith, Edell, Welter & Schmidt, P.A.

[57] ABSTRACT

A method and apparatus, suitable for in-line use, provides for determination of pre-reduction degree (PRD) of an iron oxide material, by application of a neutron inelastic scattering technique. The material is exposed to bombardment with neutrons from a source yielding the neutrons at an energy level sufficient to produce prominent gamma-rays from neutron inelastic scattering. The gamma-rays are captured and analysed to obtain an output representative of the relative weight percentages of the elements iron and oxygen, based on at least one characteristic energy level for gamma-rays emitted by those elements. The PRD for the material is determined on the basis of those weight percentages.

32 Claims, 4 Drawing Sheets

DETERMINATION OF PRE-REDUCTION DEGREE IN IRON ORE MATERIALS

This invention relates to an improved method and apparatus for determination of pre-reduction degree (PRD) of an iron oxide material.

Most iron is currently produced using a blast furnace. However blast furnaces have a number of disadvantages, namely: extensive iron ore feed preparation is required; high grade coking coal must be used; high production rates are required to be economic; and the process has limited flexibility in operation and materials use. As a result there has been a marked shift recently towards alternative methods of iron and steel production.

One move has been towards the application of direct reduction (DR) processes, often in combination with electric arc furnaces for steel production. In 1992 nearly 21 million tonnes of DRI was produced world wide from about 100 DR plants. Over 90% of the DR plants are gas-based with the remainder being coal-based. The MIDREX process is presently the most widely accepted DR method in the world, accounting for 64% of world production in 1992. The critical product quality parameters are the degree of metallisation (or the percentage of iron oxide present as metallic iron), the pre-reduction degree (or percentage of oxygen removed from the iron) and the carbon content. Gas-based DR processes usually aim to achieve metallisation levels of 85–93% and carbon contents of 1.0–2.5%. Independent control of these quantities can be achieved by selection of appropriate reduction temperature and cooling gas compositions. In coal-based DR processes carbon control is difficult to achieve. In both cases, measurement of PRD and carbon would lead to improved control of the process, particularly if able to be made on-line.

The major move has been towards the development of new smelting reduction processes such as HIsmelt and COREX. These processes involve both reduction and smelting steps. Usually a certain degree of oxygen removal is achieved in the solid state, and the remaining oxygen is removed in the liquid state. As in the case of the DR processes above, the preferably on-line measurement of pre-reduction degree and carbon in reduced iron ore would assist in the control of the process.

In its simplest form the pre-reduction degree (PRD) is defined, in relation to the highest oxidation state of $Fe_2O_3$, in terms of the iron and oxygen contents of the iron ore according to the following equation:

$$PRD = 100 - 232.7(O_{Fe}/Fe) \quad (1)$$

where $O_{Fe}$ is oxygen in the iron oxide, Fe is the total iron content (both in wt. % dry basis) and 232.7 is derived as the weight ratio of Fe to O in $Fe_2O_3$ multiplied by 100. In two component iron oxide and gangue mixtures, PRD can be expressed in terms of the total iron and oxygen contents and a factor R related to the oxygen fraction in the gangue.

A two component system (iron oxide and gangue) of course will be encountered in practice, and the parameter R therefore needs to be taken into account. For such system, PRD and R can be defined by the equations:

$$PRD = 100 - 232.7(O_{tot} - O_g)/Fe \quad (2)$$

$$R = (R_g + O_g)/O_g \quad (3)$$

where $O_{tot}$ is the total oxygen in the sample, $O_g$ is the oxygen in the gangue and $R_g$ is the remainder (ie. everything except oxygen) of the gangue.

Given that:

$$Fe + O_{Fe} + O_g + R_g = 100 \quad (4)$$

$$O_g + O_{Fe} = O_{tot} \quad (5)$$

then it can be shown that:

$$O_g = [100 - (O_{Fe} + Fe)]/R \quad \text{(from equation (4))}$$

$$O_{Fe} = (100 - PRD)Fe/232.7 \quad \text{(from equation (1))}$$

Hence: $O_g = [100 - Fe(332.7 - PRD)/232.7]/R$ and by substituting back into equation (2), we can write:

$$PRD = [R/(R-1)]*[(100 - 332.7/R) + 232.7(100/R - O_{tot})/Fe] \quad (6)$$

The pre-reduction degree can therefore be written in terms of three variables: total iron content, total oxygen content and R, the ratio of total gangue to oxygen in the gangue.

In many DR systems, there are two distinct forms of gangue, namely (i) naturally occurring gangue in the iron ore which consists primarily of silica and alumina with an R value of about 2 and (ii) flux, a large component of which is CaO for which R=3.5. From equation (6), it can be seen that, provided R remains constant, PRD will be dependent on only total iron and total oxygen contents. Hence a direct correlation can be set up between PRD and measured iron and oxygen. However, when the proportions of the two forms of gangue vary, errors will occur if R is assumed constant.

It is assumed that the amount of naturally occurring gangue (R=2) in iron ore is roughly constant, say, 7% and that the amount of added flux (R=3.5) varies from 10.2% to 12.8%, the effective value of R for the combined flux and naturally-occurring gangue varies from 2.72 to 2.82. In this case, the maximum change in calculated PRD over this range of R is 1% using total iron content of 65% and total oxygen content of 27%.

If a fixed value of R is assumed when the amount of flux varies from 10.2 to 12.8%, it is found that the calculated values of PRD only varies from the assumed mean value of 20% by ±0.7% over this range of added flux.

The reference to naturally occurring gangue includes metal oxides other than iron oxide. The metal oxides may constitute metal values to be recovered with iron in an overall smelting process, such as in the case of recovery of iron and chromium from a chromite ore. Thus, the designation of naturally occurring gangue is relative to the PRD determination, rather than necessarily relative to a smelting process for which the PRD determination is made.

The effect of non-negligible amounts of carbon on the PRD calculation formula can be determined using the modified equation below:

$$PRD = (R/R-1))*[(100 - 332.7/R) + 232.7((100 - C)/R - O_{tot})/Fe] \quad (7)$$

where C is the carbon content and all other Symbols are as defined previously. The sensitivity to carbon depends on the value of R. When the iron content is around 60% and the PRD value is about 20%, a change in carbon content of 1.0 wt. % will result in a corresponding change in calculated PRD of 3.9% for R=2 and 1.6% for R=3.5. However if the carbon content is separately measured, a correction factor can be applied to the measured PRD value.

The present invention provides an improved method and apparatus for determination of the PRD of an iron oxide ore material. At present, the most effective method is off-line chemical assay, but this is time consuming and, hence, it is not suitable for continuous monitoring of the pre-reduction and smelting stages in the production of iron or steel.

In the broadest form, the invention resides in the use of the neutron inelastic scattering (NIS) technique to determine the ratio of iron and oxygen, and optionally carbon, in a pre-reduced iron oxide material, and utilising the ratio of iron and oxygen to determine the PRD. In a process according to the invention, the iron oxide material is exposed to bombardment with neutrons, from a source yielding the neutrons at an energy level sufficient to cause nuclei of the material to produce prominent gamma-rays from neutron inelastic scattering, analysing the gamma-rays as captured by a suitable detector to obtain an output representative of the relative weight percentages of the elements iron and oxygen, and optionally carbon, based on at least one characteristic energy level for gamma-rays emitted by those elements, and determining the PRD for the material on the basis of the determined weight percent of iron and oxygen.

The invention also provides apparatus for determining the PRD of an iron oxide material, including a neutron scatter assembly having a source yielding neutrons of sufficient energy to produce inelastic scattering gamma-rays from nuclei of the material; and a detector suitable for measuring gamma-rays so produced and for providing an output representative of the count of detections of gamma-rays of at least one energy level characteristic of iron and oxygen, and optionally of carbon; the apparatus further including means for determining the PRD from the output, based on said count for each of iron and oxygen, and optionally of carbon.

The use of the NIS technique in the invention, involving bombarding a sample with fast neutrons and analysing the gamma-rays promptly emitted as the sample is being irradiated, is well suited to the analysis of elements of concentration >1 wt. % and preferably >5 wt. %. The NIS technique enables the direct measurement of Fe, $O_{tot}$ (equation (5)) and carbon, based on measuring the net peak areas of their prominent inelastic scatter gamma-rays at 0.847, 6.13 and 4.43 MeV respectively. The accuracy obtained depends on inter-element interferences, scattering cross sections and background, and high accuracy can be achieved in favourable cases. It should be noted that the NIS technique determines the total elemental concentrations present, independent of the chemical form of the elements. The NIS technique is well suited to the accurate determination of elemental ratios, as the ratio of gamma-ray yields via peak areas is much less affected by changes in bulk density or geometry than the peak areas alone. The technique has the advantages of using highly penetrating radiation so that measurements can be averaged over a large mass of sample and that measurements can be made directly on samples of large top size (eg. Up to 100 mm top size). In addition measurements can be made through the walls of vessels and simultaneous determination of many elements is possible.

As will be appreciated, the method and apparatus of the invention respectively includes suitable shielding to reduce the neutron and gamma-ray dose rates around the source to acceptable levels. Suitable shield materials contain a high hydrogen content to slow down fast neutrons; with examples being polyethylene, paraffin, water, Benelex, Lucite and various castable mixtures. In addition, shields often incorporate a proportion of either boron or lithium compounds to capture the neutrons once they are slowed down, in the present application, it is advantageous to use a shield which contains little or no oxygen, as oxygen in the shield reduces the sensitivity of the assembly oxygen in the sample. Therefore shield materials such as polyethylene are favoured for the present invention.

Any neutron source which yields neutrons of an energy level above the inelastic scattering threshold can be used. Thus, the source can be either a radioisotope source, or an electronic device such as a neutron generator or an RF linac. Neutron generators have the advantages of being able to be pulsed and being able to be turned off. However radioisotope sources are preferred as they have the advantages over neutron generators of being simpler, more stable, smaller and cheaper, and they therefor are more suited to industrial applications. A $^{238}$Pu—Be neutron source, having an output of $2\times10^7$ neutrons/sec has been useful in the context of the present invention, although other radioisotope sources can be used.

Similarly any suitable gamma-ray detector can be used. A bismuth germanate (BGO) detector is an example of a suitable detector for use in the present invention, in view of its high photopeak efficiency and low neutron capture background. However, an NaI(Tl) detector could, for example be used.

Pulses from the detector preferably are amplified by means of a suitable amplifier, such as a gain stabilised amplifier. Resultant amplified spectra then preferably are processed using a suitable computer with which count rates for selected peaks are generated. Net count rates for those peaks may be determined by combining the count rates from a window around each peak of interest and one or more windows around nearby areas in the spectrum. Until overall procedure is established for a given pre-reduced material, the most favourable window settings may be chosen from correlation of the parameter of interest (ie. iron and oxygen contents, and optionally the carbon content) as determined by chemical assay. With establishment of the procedure, the net count rates are used with application of a suitable equation, such as equation (1), (6) or (7), to produce an output indicating the determined PRD.

In general, the application of on-line analysis techniques in the DR and smelting industry is difficult. The iron oxide material usually is in large vessels having thick steel walls which essentially render the material inaccessible to techniques having low penetrating ability. Also, the high temperatures involved are not suitable for use of temperature sensitive devices for which cooling to acceptable levels is not practical. Also, the temperatures and inimical nature of the hot iron oxide material can make devices relying on insertion of a probe in the material unacceptable. However, the NIS technique relies on highly penetrating radiation and while cooling is required to maintain the temperature of the detector at acceptable levels, it readily can be used for on-line analysis in DR and smelting.

Requirements for a satisfactory location of the neutron scatter assembly include:

a sufficient thickness of iron oxide material, preferably greater than about 200 mm;

a minimal wall thickness through which the NIS technique is to be performed;

a wall material containing a minimum of iron and aluminium;

a minimal temperature to which the assembly is exposed;

access to a quantity of iron oxide material which is representative of the whole;

an ability to obtain iron oxide materials, when required, for off-line chemical assay;

and a lack of physical obstacles so that the assembly can be installed.

Also, as indicated, a facility for maintaining the detector temperature at acceptable levels is required. However, despite these matters, there are a number of possibilities for location of the neutron scatter assembly in DR and smelting plants.

One arrangement is to mount the assembly near the throat or a side of a hopper or the like. Where the iron oxide material flows through the hopper and the assembly is adjacent to a side wall, it is necessary that the flow at that wall is representative of the total material stream. Alternatively, the assembly can be located adjacent to a conveyor, chute or the like by which the iron oxide is passed from a pre-reduction furnace or reactor to a smelting furnace or reactor. A further alternative is for a bulk sample of the iron oxide material to be automatically extracted from a process stream, analysed in accordance with the invention, and then returned to the stream.

The invention now will be illustrated with reference to the accompanying drawings and the following Examples. In the drawings.

EXAMPLE 1

Figure 1:
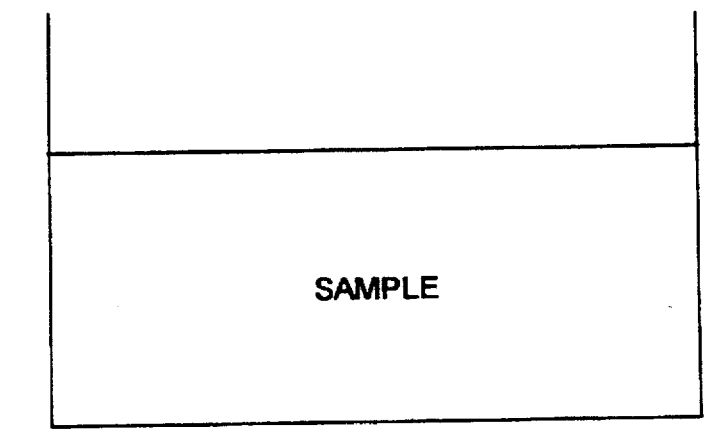
FIG. 1 is a schematic representation of one arrangement for a NIS assembly, as used in laboratory analysis.

NIS determinations were made using the arrangement of FIG. 1. In this, an open-top aluminium box 10 of dimensions 395 along each side and 290 mm high was used as a container for bulk iron oxide ore samples 12. Box 10 had walls of 3 mm thickness. A neutron scatter assembly 14 was mounted below the box for the determinations. As shown, assembly 14 comprised a $^{238}$Pu—Be neutron source 16 and a bismuth germanate detector 18. A BGO detector was selected for the reasons given earlier herein. A $^{60}$Co source (not shown) was fixed to the front of detector 18 for the purpose of calibration and stabilisation. Also tungsten block 20 was positioned between source 16 and detector 18 to prevent the 4.43 MeV gamma-rays emitted by source 16 from reaching detector 18.

Gamma-ray spectra induced by bombardment of a sample 12 by neutrons from source 16 were collected by detector 18. The lateral spacing between source 16 and detector 18 below box 10, as will be appreciated, resulted in detection of back-scattered gamma-rays. The output of detector 18 is passed to a remote computer (not shown) for analysis of gamma-ray spectra, and determination of PRD.

Quantities of nine iron oxide materials, derived from different ores, were used as respective samples 12. These ranged in PRD from 0 to 23.4%. The particle size for each material was less than 1 mm. In addition to NIS analysis, a laboratory assay was performed on each of the materials for PRD, Fe, CaO and MgO.

Two sets of data were collected from a respective sample 12 based on each of the nine different iron oxide materials. For the first of these sets, box 10 was filled with a 29.0 kg sample 12 of each material in turn. The samples were well mixed and, after being filled with each sample 12, box 10 was dropped on the floor several times to ensure uniform packing of the sample. For the second set, no mixing or packing was done.

EXAMPLE 2

Figure 2:
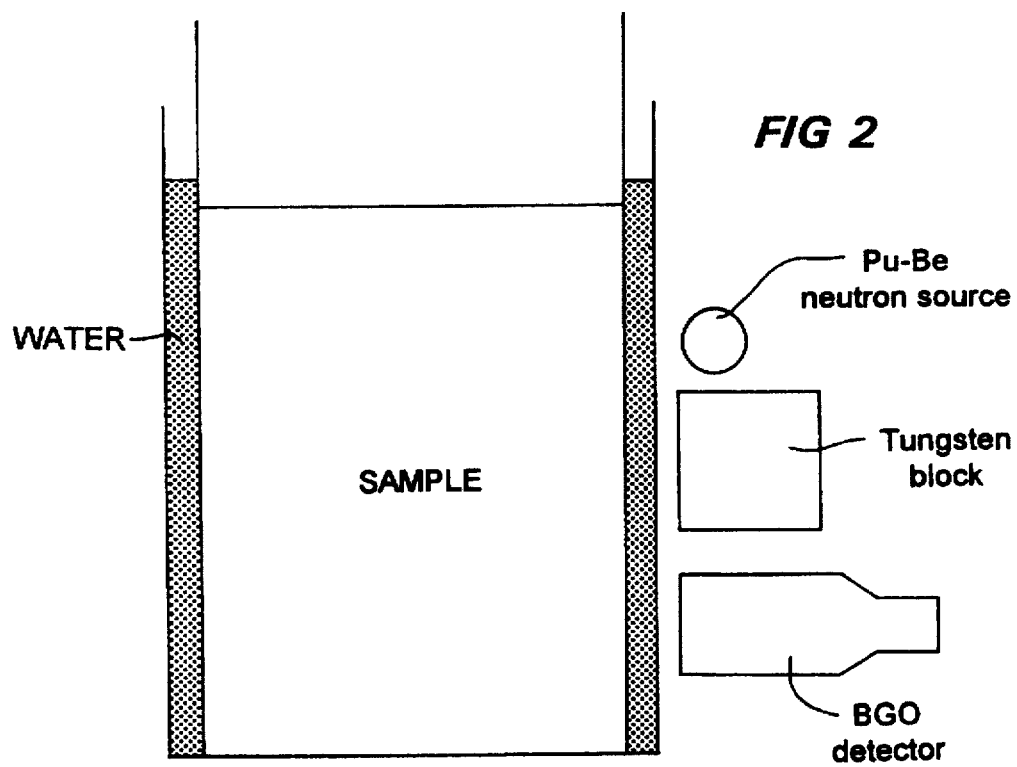
FIG. 2 is a schematic representation of a second arrangement.

The general procedure of Example 1 was repeated, but using the arrangement of FIG. 2. In that arrangement, box 10 was replaced by a cylindrical vessel 30 in the form of a double-walled pipe closed at the base. Both of the pipes and the base were of 6 mm thickness, while the respective integral diameters of the inner and outer pipes was 200 and 230. Coolant water 32 was supplied to the 9 mm gap between the pipes.

The tests conducted with the FIG. 2 arrangement were static, as with those of FIG. 1. However, the geometry for FIG. 2 was designed to simulate an arrangement in which hot iron oxide material was passed through the inner pipe, for ascertaining the extent of the influence of a coolant. In this regard, it should be noted that with testing of hot iron oxide material, BGO detector 18 would need to be maintained at a temperature below about 25° C. for satisfactory operation.

In the FIG. 2 arrangement, the $^{238}$Pu—Be neutron source 16, the BGO detector 18 and tungsten block 20 were vertically disposed, adjacent to the outer surface of the outer pipe of vessel 30. Again, operation was by back-scattering of gamma-rays from sample 12. Again, in the FIG. 2 arrangement, the output of detector 18 is able to be passed to a remote computer (not shown) for analysis of gamma-ray spectra and PRD determination.

The FIG. 2 arrangement was used with respective vessels 30 made of different materials, including Monel, stainless steel, aluminium and tin.

Four sets of data were collected with the FIG. 2 arrangement again based on respective 29.0 kg samples 12 of the nine different iron oxide materials ranging in PRD from 0 to 23.4%, and having a particle size less than 1 mm. Two sets were based on samples which were well mixed and packed as in Example 1, while two sets were with samples which were not mixed or packed.

Figure 3:
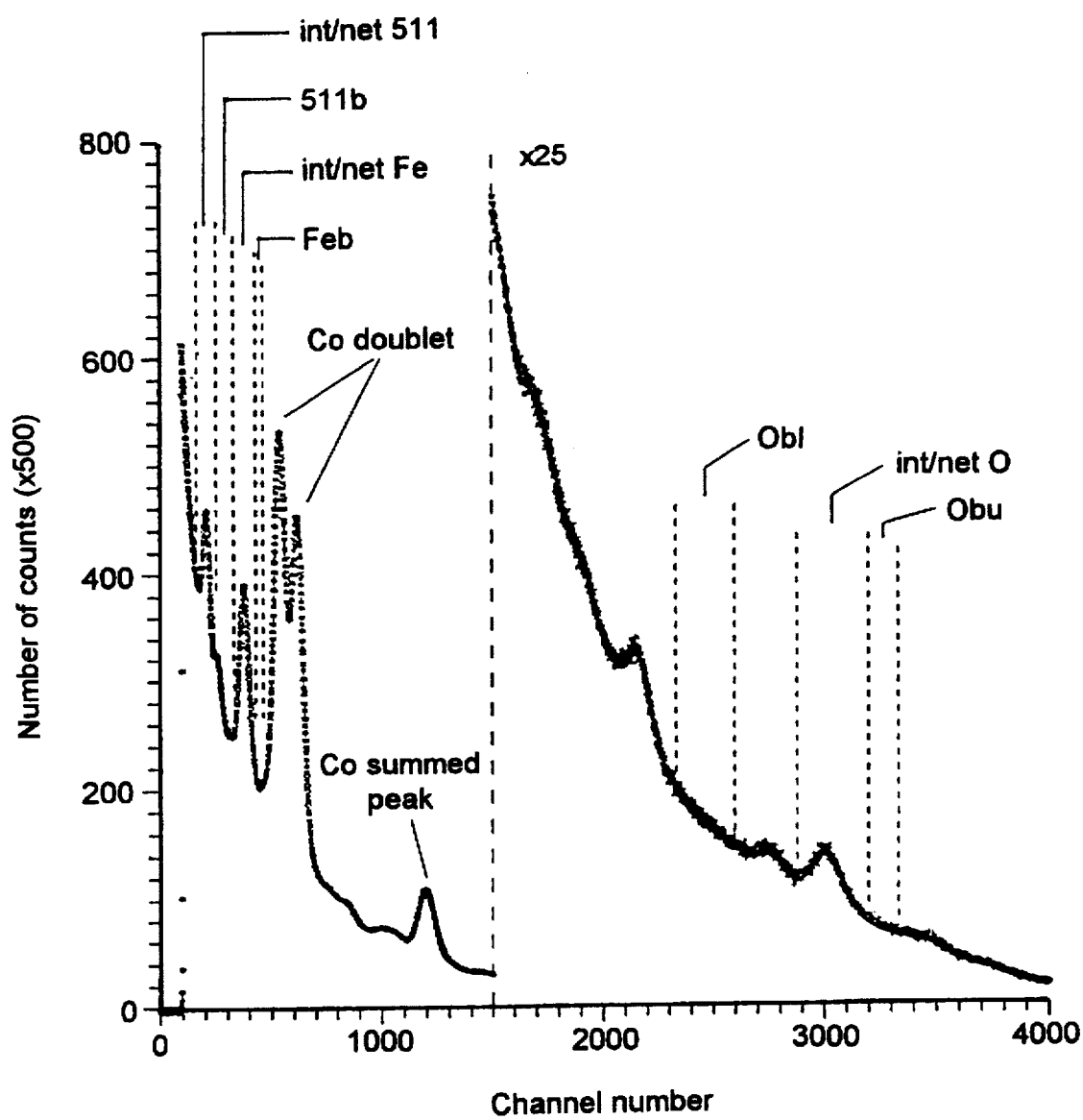
FIG. 3 shows a typical spectrum obtained with analysis by the arrangement of FIG. 1.
Figure 4:
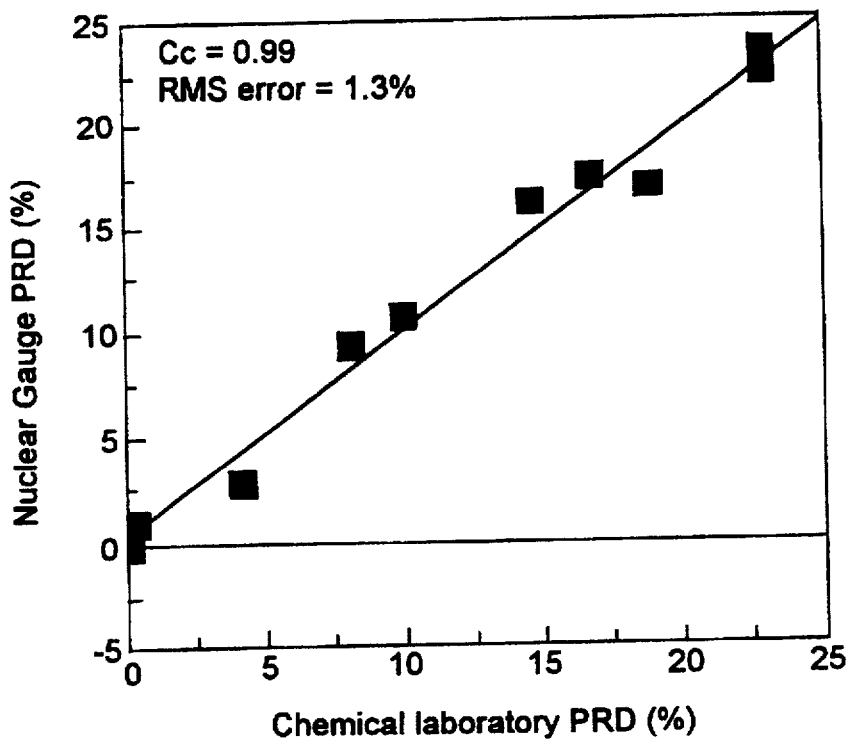
FIG. 4 is a graphical representation providing a comparison of PRD determinations obtained with analysis by the arrangement of FIG. 1 and chemical assay.
Figure 5:
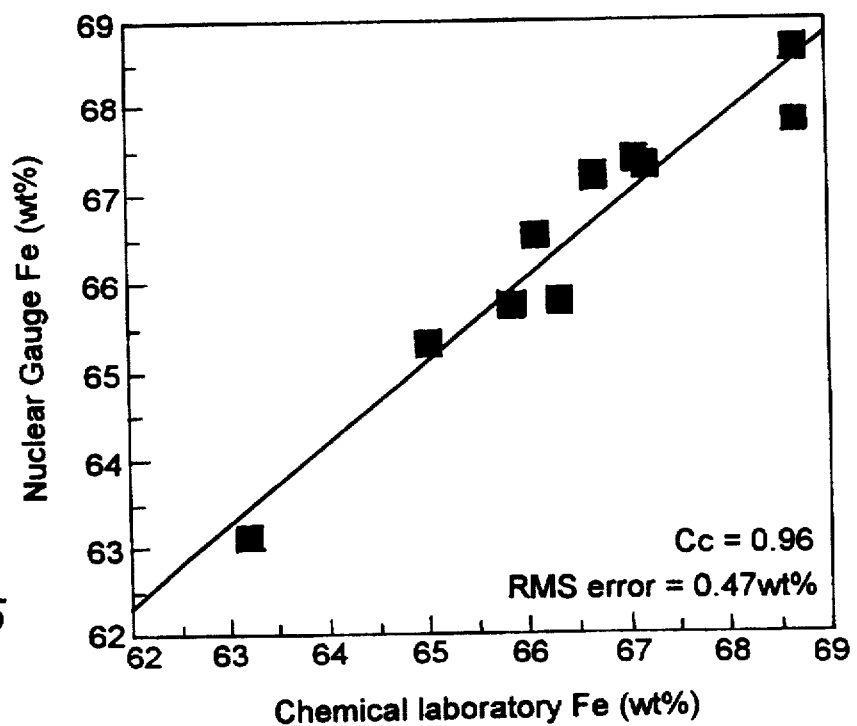
FIG. 5 is a graphical comparison of iron content determinations relevant to the analysis and assay of FIG. 4.

Results obtained with the FIG. 1 arrangement are illustrated by FIGS. 3 to 5.

A typical spectrum obtained with NIS analysis, according to the arrangement of FIG. 1. is shown in FIG. 3. In FIG. 3, the right hand spectra section represents 25 times magnification compared with the left hand spectra section. The major peaks of interest are the 511 keV gamma-ray from pair production, the 847 keV gamma-ray from iron, and the 6.13 MeV gamma-ray from oxygen. These peaks are highlighted in FIG. 3 by the selected windows shown respectively as "int/net 511", "int/net Fe" and "int/net". FIG. 3 also shows peaks resulting from use of the $^{60}$Co source.

Appropriate channel regions, as shown in FIG. 3, were selected for the peaks of interest and related background areas. Correlation involving the gross number of counts for each of these regions, a well as the net area of peaks as calculated by software employed with a microprocessor associated with assembly 14, were carried out using multiple linear regression to ascertain the accuracy with which the PRD and total Fe could be determined.

For the Example 1/FIG. 1 arrangement in which samples 12 were packed, the correlation of PRD to int Fe, int O, FeB, Obl and Obu (see FIG. 3) was found to give the best results with a correlation coefficient of 0.99 and an RMS error of 1.3% for the set of nine samples 12. This is illustrated graphically in FIG. 4. In contrast the best correlation results, for the data set for the Example 1/FIG. 1 arrangement in which samples 12 were not packed, gave an RMS error of 3.2% for PRD. Similar trends were obtained with the total Fe correlations. As shown in FIG. 5, a correlation coefficient of 0.97 and RMS error of 0.47 wt. % was obtained for the Example 1/FIG. 1 arrangement with packed samples 12.

Similar results were obtained in Example 2, using vessel 30 and the geometry shown in FIG. 2, for vessels 30 containing a minimum of iron and aluminium.

The results obtained with Examples 1 and 2 indicate that PRD can be determined, using the NIS technique, with a precision of the order of about 1 to 1.5%, and with a precision for total iron of about 0.5 wt. %. However, those results also show that the accuracy of the method can be substantially affected by both nonuniformities in sample packing and in the vessel material.

EXAMPLE 3

Figure 6:
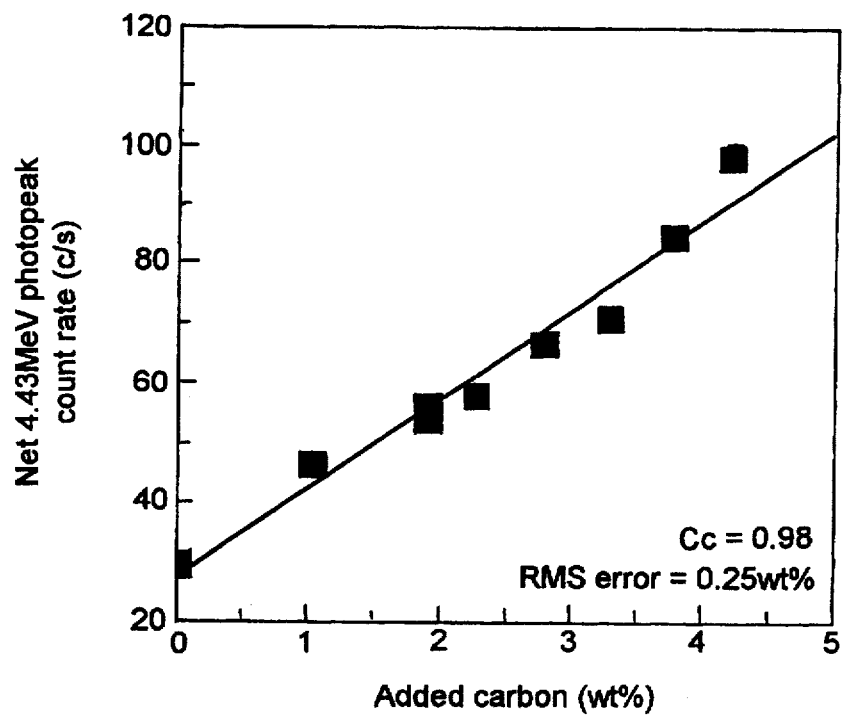
FIG. 6 is a graphical representation of MeV count rate versus added carbon, obtained with use of the arrangement of FIG. 1.

The accuracy of carbon determination by the NIS technique was tested, using an iron oxide material with seven respective amounts of added powdered graphite up to a maximum of 4.2 wt. % C. This was in accordance with the procedure of Example 1/FIG. 1, using 29.0 kg samples and packing. The net number of counts, obtained by subtracting a linear background from the gross number of counts in the 4.43 MeV carbon peak, was extracted from each spectrum obtained from BGO detector 18. The results, summarised by FIG. 6, show RMS error for carbon determination was 0.25 wt. % C.

As will be appreciated from the foregoing, the invention provides a method and apparatus for quantitatively determining the PRD of an iron oxide ore material. In relation to this, it is to be appreciated that the neutron scatter assembly used in the invention can be provided in a variety of geometries, in the back-scatter arrangement illustrated in each of FIGS. 1 and 2, the neutron source and detector are on the same side of and external to the iron oxide material for which a determination is made. However, they can be surrounded by the material, such as within an annular flow of the material. Also, the source and detector can be on opposite sides of the iron oxide material, whether this be with both the source and detector external to the material or one of them, preferably the source, housed within the material.

The invention also can be used to simultaneously determine other elements present. This has been illustrated by reference to carbon. However, in the context of iron oxide material, another relevant element can be chromium, frequently present as mixed iron and chromium oxide in iron oxide ore materials. In the latter regard, it will be appreciated that it can be relevant, in determining PRD, to consider pre-reduction with respect to both iron oxide and chromium oxide constituents, or mixed oxide in the case of material such as a chromite ore.

It also is to be appreciated that, for many iron oxide ores, the overall composition is substantially constant, with the initial iron and oxygen content known with a reasonable level of accuracy. Also, in the course of pre-reduction, particularly where this is by use of a reducing gas, the change in the iron oxide material essentially can entail loss of only oxygen to the gas phase. Given these matters, it therefore is within the scope of the present invention to utilise the NIS technique solely to determine the oxygen content after pre-reduction. Knowing the initial ratio of iron and oxygen contents and the content of oxygen following pre-reduction, it remains possible to determine the PRD.

The invention extends to the determination of PRD In the context of an operation for pro-reducing and smelting iron ore. However, the invention also extends to a further method and installation for the production of iron or steel, including an alloy steel such as ferro-chromium.

In the context of such further production method or installation, the invention may use a pre-reduction unit which comprises a furnace or reactor operable to procedure iron-ore received therein, a smelting unit which comprises a furnace or reactor operable to smelt pre-reduced ore produced in the pre-reduction unit, and transfer means operable for enabling transference of the pre-reduced ore from the pre-reduction unit to the smelting unit. In that context, the invention additionally requires apparatus for determining the PRD of an iron oxide material, as detailed above, and means for mounting the neutron scatter assembly of that apparatus at a location on or adjacent to the transfer means for determination of the PRD of the prereduced ore prior to the latter being received in the smelting unit. The mounting means most preferably is such as to position the neutron scatter assembly for on-line determination of the PRD.

Figure 7:
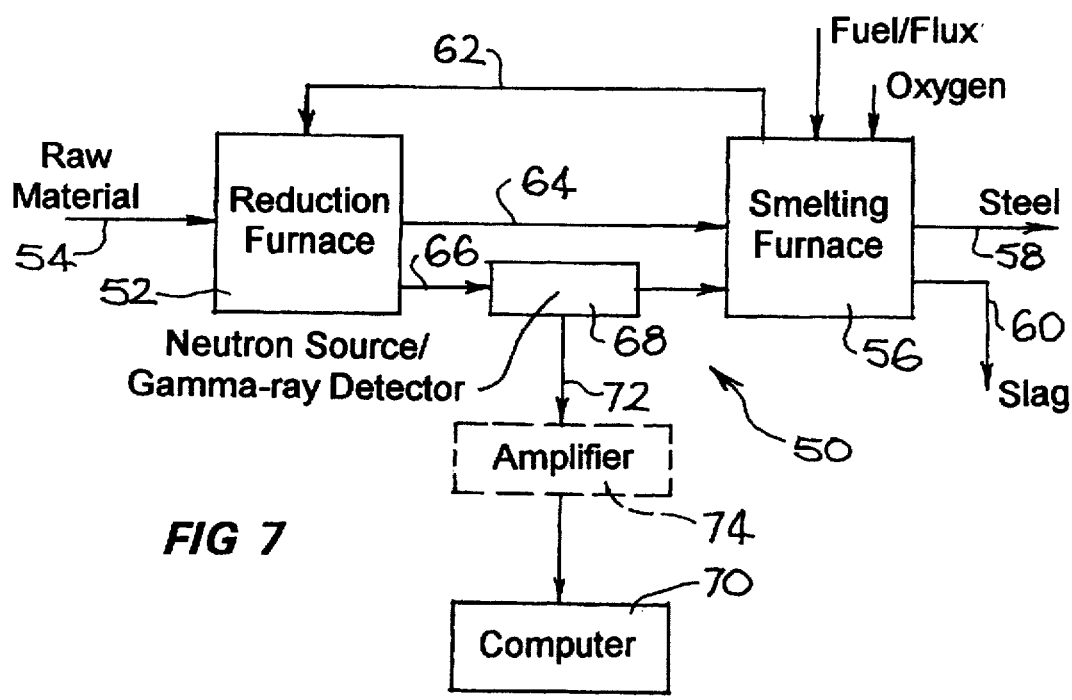
FIG. 7 is a flow chart, schematically illustrating an installation for the production of steel, based on use of apparatus according to the invention.

A suitable installation 50, based on use of the apparatus of the present invention, is shown in FIG. 7. Installation 50 includes a pre-reduction furnace 52 to which iron-ore feed material is charged from a suitable source, as depicted by line 54. In furnace 52, the ore is partially pre-reduced to a required degree, before passing to smelting furnace 56 in which the pre-reduced material is smelted to steel with the supply of fuel, flux and oxygen-containing gas as shown. The steel product, and slag produced during smelting is tapped, from furnace 56 when required, as depicted by lines 58 and 60. Off-take gases from furnace 56 are reducing, due to their content of CO and $H_2$, and these are passed to furnace 52 via line 62 and can provide the sole or principal reductant for achieving pre-reduction in furnace 52.

All, or a representative part, of the partially pre-reduced feed material passes from furnace 52 to furnace 56 via line 66 in which it is subjected to in-line NIS technique analysis, using apparatus according to the invention comprising neutron scatter/gamma-ray detector assembly 68 and remote computer 70. Where only a representative part of the feed material passes to furnace 56 via line 66, the balance passes via line 64. However, in an alternative arrangement, line 66 may be in a closed loop which returns the material to furnace 52, with material passing from furnace 52 to furnace 56 only via line 64.

The arrangement for assembly 68 may be similar to the arrangement of FIG. 2. That is, assembly 68 may comprise a water-cooled section of line 66, adjacent to which a neutron source and gamma-ray detector of assembly 68 are positioned. The arrangement may provide for operation by back-scattering of gamma-rays generated by bombardment of pre-reduced material passing through line 66 by neutrons from the source of assembly 68, with the output from the detector of assembly 68 passing via line 72 to computer 70. Computer 70 is operable to count the rates for selected peaks of spectra generated by the detector and, using an appropriate one of the equations (1), (6) or (7), to determine the PRD of the pre-reduced material. The computer may receive amplified spectra from the detector, by provision of a gain stabilised amplifier 74 in line 72. Also, the output of PRD provided by computer 70 can be used to control operation of furnace 52 and/or furnace 56 so as to maintain pre-reduction in furnace 52 as the required level and hence, overall efficiency of operation of Installation 50 in its production of steel.

The apparatus for determining PRD in the further method or installation of the invention can be adapted for the control of operation of one or both of the pre-reduction and smelting units. In the pre-reduction and smelting of iron ore, it is usual for gases generated in the smelting unit to be used as at least part of reductant required to be supplied for pre-reduction in the pre-reduction unit. This can be the case whether or not those gases are partially post-combusted in the smelting unit to increase the level of heat energy available for smelting. Economic operation of the overall pre-reduction/smelting procedures necessitates close control over various parameters, such as:

- the feed rates for ore and reductant to the pre-reduction unit;
- the temperature at which pre-reduction is achieved;
- the PRD required and the accuracy with which this is obtained;
- the feed rates to the smelting unit for pre-reduced ore, fuel/reductant, flux and oxygen for smelting and for post-combustion;
- the melt temperature prevailing in the smelting unit;
- the temperature of gases exhausted from the smelting unit; and
- the overall materials and heat energy balance.

Accurate on-line determination of PRD enables ongoing adjustment, as required, of operation in the pre-reduction unit for maintenance of a required PRD, such as for example, to 30 or 60%. However, that accurate determination of PRD also enables adjustment, as required, of operation in the smelting unit. Indeed, given the inter-dependence of operation in the two units for overall optimisation of economic production of iron or steel, inter-related control typically is required in each unit.

Finally, it is to be understood that various other modifications and/or alterations may be made without departing from the spirit of the present invention as outlined herein.

We claim:

1. A process for determining the pre-reduction degree (PRD) of pre-reduced iron oxide material, wherein a neutron inelastic scattering technique is applied to the material by the steps of:
   (i) exposing the material to bombardment with neutrons, from a source yielding the neutrons at an energy level sufficient to cause nuclei of the material to produce prominent gamma-rays from neutron inelastic scattering;
   (ii) capturing, by use of a suitable detector, gamma-rays so produced;
   (iii) analysing the captured gamma-rays to obtain an output representative of the relative weight percentages of the elements iron and oxygen, based on at least one characteristic energy level for gamma-rays emitted by those elements; and
   (iv) determining the PRD for the material on the basis of the determined weight percentage of iron and oxygen.

2. The process of claim 1, wherein said material substantially comprises pre-reduced iron oxide and wherein the material consists of two components of iron oxide and gangue; and wherein analysis is based on measuring the net peak areas of prominent inelastic scattered gamma-rays at 0.847 MeV for iron and 6.13 MeV for oxygen, and determining PRD for the material based on the equation:

$$PRD = 100 - 232.7(O_{Fe}/Fe)$$

where $O_{Fe}$ is the oxygen content of the material and Fe is the iron content of the material.

3. The process of claim 1, wherein the material consists of two components of iron oxide and gangue; and wherein analysis is based on measuring the net peak areas of prominent inelastic scattered gamma-rays at 0.847 MeV for iron and 6.13 MeV for oxygen, and determining PRD for the material based on the equation:

$$PRD = [R/(R-1)]*[(100-332.7/R)+232.7(100/R-O_{tot})/Fe]$$

where Fe is the total iron content of the material, $O_{tot}$ is the total oxygen content of the material and R is a factor related to the oxygen fraction in the gangue.

4. A process according to claim 1, wherein the material consist of the three components of iron oxide, naturally occurring gangue and gangue-type constituent resulting from flux; and wherein the analysis is based on measuring the net peak areas of prominent inelastic scattered gamma-rays at 0.847 MeV for iron and 6.13 MeV for oxygen, and determining PRD for the material based on the equation:

$$PRD = [R/(R-1)]*[(100-332.7/R)+232.7(100/R-O_{tot})/Fe]$$

where $O_{tot}$ is the oxygen content of the material, Fe is the iron content of the material and R is a factor related to the oxygen fraction in the naturally occurring gangue and the gangue-type constituent.

5. A process according to claim 1, wherein the material contains carbon and, apart from the carbon content, consists of at least two components of iron oxide, naturally occurring gangue and optionally gangue-type constituent resulting from flux; and wherein the analysis is based on measuring the net peak areas of prominent inelastic scattered gamma-rays at 0.847 MeV for iron, 6.13 MeV for oxygen and 4.43 MeV for carbon, and determining the PRD for the material based on the equation:

$$PRD = (R/R-1))*[(100-332.7/R)+232.7((100-C)/R-O_{tot})/Fe]$$

where Fe is the total iron content of the material, $O_{tot}$ is the total oxygen content of the material, C is the carbon content of the material, and R is a factor related to the oxygen fraction of the gangue plus any gangue-type constituent.

6. The process of claim 1, wherein shielding material is provided around the neutron source to reduce the neutron and gamma-ray dose rates around the source to acceptable levels, the shielding material having a high hydrogen content to slow down fast neutrons.

7. The process of claim 6, wherein the shielding material is selected from paraffin, water, and plastics materials including polyethylene, Benelex, Lucite and castable mixtures.

8. The process of claim 6, wherein the shielding material incorporates a compound of boron or lithium providing for capture of slowed neutrons.

9. The process of claim 6, wherein the shielding material is substantially free of oxygen.

10. The process of claim 1, wherein the neutron source used is a radioisotope source, such as a $^{238}$Pu—Be source.

11. The process of claim 1, wherein the neutron source used is an electronic device operable as a neutron generator.

12. The process of claim 1, wherein the neutron source used is an RF linac.

13. The process of claim 1, wherein the gamma-ray detector used is a bismuth germanate detector.

14. The process of claim 1, wherein the gamma-ray detector used is an NaI(Tl) detector.

15. The process of claim 1, wherein pulses comprising the output from the detector are amplified by means of a suitable amplifier, and resultant amplified spectra then are processed using a suitable computer with which count rates for selected peaks are generated, and net count rates are used to produce an output indicative of PRD.

16. The process of claim 1, wherein said steps are conducted in-line, in a direct reduction process for the production of iron or steel product, intermediate a pre-reduction furnace in which iron oxide feed material is subjected to a partial reduction to produce the pre-reduced material, and a smelting furnace in which the pre-reduced material is smelted to produce the iron or steel product; and wherein the pre-reduced material is subjected to said steps as it passes from the pre-reduction furnace to the smelting furnace.

17. Apparatus for determining the pre-reduction degree (PRD) of pre-reduced iron oxide material, wherein the apparatus enables a neutron inelastic scattering technique and comprises:

(i) a neutron scatter assembly including a neutron source for yielding neutrons of sufficient energy to produce inelastic scattering gamma-rays from nuclei of the material exposed to said neutrons;

(ii) a detector suitable for measuring gamma-rays so produced and for providing an output representative of count detections of at least one energy level characteristic for iron and oxygen; and (iii) processing means for analysing the output and for determining the PRD at least on the basis of said count for oxygen where the iron content of said materials is known or on the basis of said counts for iron and oxygen.

18. The apparatus of claim 17, further including amplifier means suitable for amplifying output pulses from the detector to provide amplified spectra which are processed by a computer comprising said processing means.

19. The apparatus of claim 17, wherein the material substantially comprises pre-reduced iron oxide material; and wherein said processing means is operable to provide analysis based on measuring net peak areas of prominent inelastic scattered gamma-rays at 0.847 MeV for iron and 6.13 MeV for oxygen and to determine PRD for the material based on the equation:

$$PRD=100-232.7(O_{Fe}/Fe)$$

where $O_{Fe}$ is the oxygen content of the material and Fe is the iron content of the material.

20. The apparatus of claim 17, wherein the material consists of two components of iron oxide and gangue constituent; and wherein said processing means is operable to provide analysis based on measuring peak areas of prominent inelastic scattered gamma-rays at 0.847 MeV for iron and 6.13 MeV for oxygen and to determine PRD for the material based on the equation:

$$PRD=[R/(R-1)]*[(100-332.7/R)+232.7(100/R-O_{tot})/Fe]$$

where Fe is the total iron content of the material, $O_{tot}$ is the total oxygen content of the material and R is a factor related to the oxygen fraction in the gangue.

21. The apparatus of claim 17, wherein the material contains carbon and, apart from carbon content, consists of two components of iron oxide and gangue constituent; and wherein said processing means is operable to provide analysis based on measuring peak areas of prominent inelastic scattered gamma-rays at 0.847 MeV for iron, and 6.13 MeV for oxygen and 4.43 MeV for carbon, and to determine PRD for the materials based on the equation:

$$PRD=(R/R-1))*[(100-332.7/R)+232.7((100-C)/R-O_{tot})/Fe]$$

where Fe is the total iron content of the materials, $O_{tot}$ is the total oxygen content of the materials, C is the carbon content of the materials, and R is a factor related to the oxygen fraction of the gangue constituent.

22. The apparatus of claim 20, wherein the gangue constituent consists of naturally occurring gangue and gangue-type constituent resulting from flux, and wherein R is a factor related to the oxygen fraction in the naturally occurring gangue and the gangue type constituent.

23. The apparatus of claim 17, further including shielding material around the neutron source to reduce the neutron and gamma-ray dose rates around the source to acceptable levels, the shielding material having a high hydrogen content to slow down fast neutrons.

24. The apparatus of claim 23, wherein the shielding material is selected from paraffin, water, and plastics materials including polyethylene, Benelex, Lucite and castable mixtures.

25. The apparatus of claim 23, wherein the shielding material incorporates a compound of boron or lithium providing for capture of slowed neutrons.

26. The apparatus of claim 23, wherein the sheilding material is substantially free of oxygen.

27. The apparatus of claim 17, wherein the neutron source is a radioisotope source such as a $^{238}$Pu—Be source.

28. The apparatus of claim 17, wherein the neutron source used is an electronic device operable as a neutron generator.

29. The apparatus of claim 17, wherein the neutron source is an RF linac.

30. The apparatus of claim 17, wherein the detector is a bismuth germanate detector.

31. The apparatus of claim 17, wherein the detector is an NaI(Tl) detector.

32. The apparatus of claim 17, wherein said neutron source and said detector are mounted, in a direct reduction smelter installation for the production of iron or steel, intermediate a pre-reduction furnace of the installation operable to partially reduce iron oxide feed material and a smelting furnace of the installation operable to smelt the pre-reduced material to iron or steel, whereby the apparatus is operable to provide in-line determination of PRD of material passing from the pre-reduction furnace to the smelting furnace.

* * * * *